(12) United States Patent
Chen et al.

(10) Patent No.: US 12,119,123 B2
(45) Date of Patent: Oct. 15, 2024

(54) SYSTEMS AND METHODS USING BLOCKCHAIN FOR IN-VEHICLE HEALTH AND WELLNESS TRACKING

(71) Applicant: Ford Global Technologies, LLC, Dearborn, MI (US)

(72) Inventors: Jay Z. Chen, Sylvania, OH (US); Matthew Cassoli, Dearborn, MI (US); Pramita Mitra, West Bloomfield, MI (US); Josh Fodale, Ypsilanti, MI (US); Spencer White, Dearborn, MI (US); John Wayne Jaranson, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 496 days.

(21) Appl. No.: 17/497,767

(22) Filed: Oct. 8, 2021

(65) Prior Publication Data

US 2023/0111974 A1 Apr. 13, 2023

(51) Int. Cl.
*G16H 70/60* (2018.01)
*G01C 21/34* (2006.01)
*G16H 50/20* (2018.01)
*H04L 9/32* (2006.01)

(52) U.S. Cl.
CPC ......... *G16H 70/60* (2018.01); *G01C 21/3438* (2013.01); *G01C 21/3484* (2013.01); *G16H 50/20* (2018.01); *H04L 9/3265* (2013.01)

(58) Field of Classification Search
CPC ............................ G16H 50/20; G01C 21/3438
USPC ......................................................... 713/156
See application file for complete search history.

(56) References Cited

U.S. PATENT DOCUMENTS

| 6,330,499 B1 | 12/2001 | Chou et al. |
| 11,919,539 B2 * | 3/2024 | Wolff .................. G06V 40/168 |
| 2019/0378352 A1 | 12/2019 | Dey et al. |

FOREIGN PATENT DOCUMENTS

CN 112446761 A 3/2021

OTHER PUBLICATIONS

Pontus Larsson, Ph.D, "User Experience Of On-Demand Autonomous Vehicles", IctechAB, Goteborg, Jun. 21, 2021, 17 pages.
Sarwant Singh, "Health, Wellness And Well-Being Features In Cars To Accelerate Due To Covid 19", www.forbes.com; Mar. 30, 2020, 8 pages.

* cited by examiner

*Primary Examiner* — Lan Dai T Truong
(74) *Attorney, Agent, or Firm* — Emily Drake; Eversheds Sutherland (US) LLP

(57) ABSTRACT

This disclosure describes systems and methods using blockchain for in-vehicle health and wellness tracking. An example method may include receiving a request for a vehicle from a mobile device of a user. The example method may also include receiving, from a pathogen detector device within a first vehicle, an indication that a number of pathogens within the first vehicle is less than a threshold amount. The example method may also include assigning the first vehicle to the user based on the indication that the number of pathogens within the first vehicle is less than a threshold amount.

20 Claims, 11 Drawing Sheets

SYSTEMS AND METHODS USING BLOCKCHAIN FOR IN-VEHICLE HEALTH AND WELLNESS TRACKING

BACKGROUND

The exposure of airborne micro-particles such as viral and bacterial pathogens can pose an epidemiological concern in our society, causing a variety of infections, respiratory illnesses, and transmissible diseases such as COVID-19. With the rising use of the vehicle as a shared resource e.g., ride sharing, car rental, shared fleet vehicles, etc., the possible transmission of such micro-particles is a concern. There are different potential solutions for identifying airborne micro-particles and sanitizing or cleaning them. There is no standard way today to disseminate the output of these solutions (i.e., the vehicle interior air quality status) to different stakeholders.

BRIEF DESCRIPTION OF THE DRAWINGS

The detailed description is set forth with reference to the accompanying drawings. The use of the same reference numerals indicates similar or identical components or elements; however, different reference numerals may be used as well to indicate components or elements which may be similar or identical. Various embodiments of the disclosure may utilize elements and/or components other than those illustrated in the drawings, and some elements and/or components may not be present in various embodiments. Depending on the context, singular terminology used to describe an element or a component may encompass a plural number of such elements or components and vice versa.

DETAILED DESCRIPTION

Figure 1:
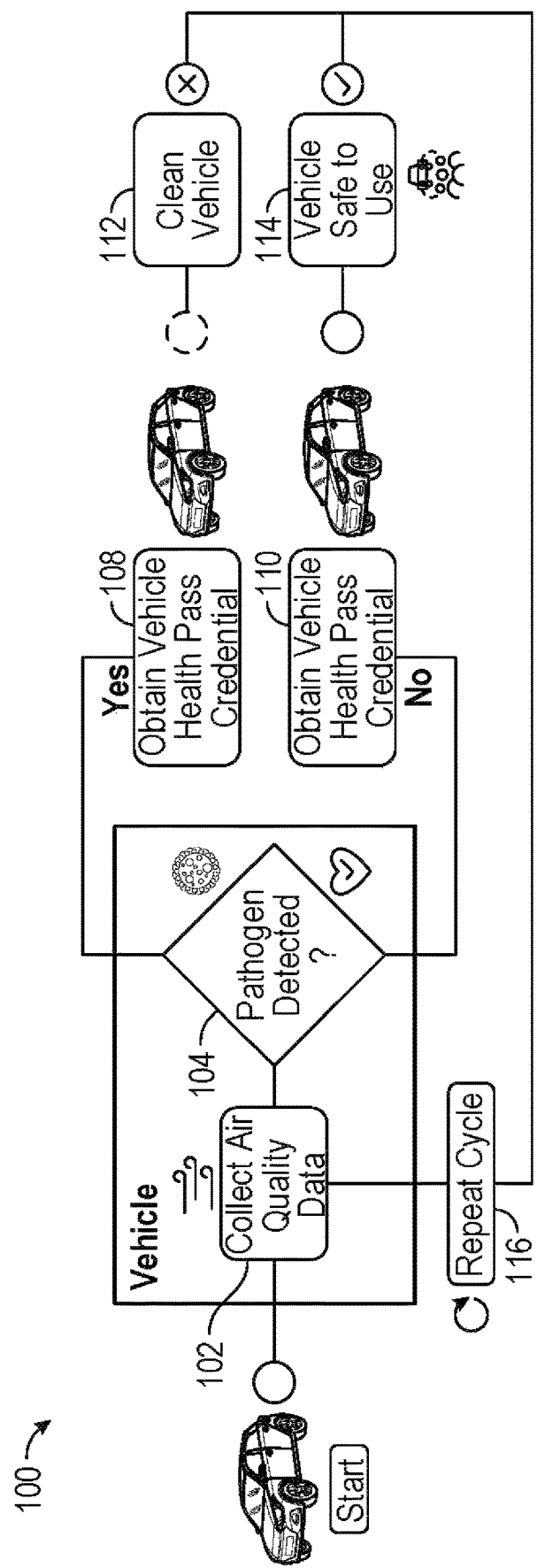
FIG. 1 illustrates an example flowchart, in accordance with one or more embodiments of the disclosure.

This disclosure relates to, among other things, systems and methods using Blockchain for in-vehicle health and wellness tracking. Particularly, the systems and methods described herein may be used in the context of ride hail services to ensure that vehicles are clean for successive passengers. The systems and methods may also allow a ride hail rider to request a vehicle cleanliness status check, and request a different vehicle if a currently-assigned vehicle does not meet a cleanliness requirement. While reference may be made to ride hail services herein, the systems and methods may also be applicable in other contexts as well. For example, the systems and methods may also be applicable to vehicle fleet management and vehicle rentals as well, to name a few non-limiting examples.

To accomplish the in-vehicle health and wellness tracker, a pathogen detector may be integrated within the vehicle. A pathogen detector may be a device that may be a standalone device or a device that is integrated into a vehicle. The pathogen detector may be capable of detecting bacterial and viral pathogens within a given environment, such as the interior of the vehicle. The pathogen detector may also be capable of transmitting collected data to a separate local or remote system for processing. The pathogen detector may include a direct air handling system for collecting airborne samples. The pathogen detector may include a biochip and/or a biosensor for detecting the presence of a pathogen. The pathogen detector may also include an integrated control module with embedded software. The pathogen detector may be housed within an integrated housing assembly for installation into vehicle interior cabin such as the center console. The air handling system may trap airborne pathogens from within the vehicle environment and allow binding to a nanoprobe on a surface of the biochip. The pathogen detector may then read the optical characteristics of the biochip and output signals to the control module or to an external device app. The software in the control module or external device app may interpret the signals and output wireless data indicative of a level of pathogens found within the vehicle.

The pathogen detector may continuously (or periodically) analyze the air quality of the vehicle. When pathogen micro-particles are detected, a vehicle health pass credential may be requested from the Blockchain. A vehicle health pass credential may be a digital certificate issued to the vehicle using the W3C Verifiable Credentials standard, for example. To that end, the vehicle may have its own Blockchain-based Self-Sovereign Identity (SSI) using the W3C Decentralized Identifier (DID) standard. In the DID ecosystem, verifiable credentials can be issued by anyone, about anything, and can be presented to and verified by everyone. In case of the vehicle health pass credential use-case, the verifiable credential may be issued to the vehicle, which may be the holder that stores it for later use. The credential may be issued by the OEM or a trusted third-party, which may be the issuer. Verifiable credentials may be digitally signed by the issuer, which may make them tamper-resistant and instantaneously verifiable, allowing the holder to prove something about themselves (e.g., in-vehicle air quality status) by presenting their credentials to a verifier (e.g. the rider).

If any pathogens are detected, or if the number of pathogens exceeds the threshold amount (if applicable), then the vehicle may also be sent to a cleaning facility for cleaning. Alternatively, the vehicle may include internal cleaning mechanisms that may allow the vehicle to clean itself on the spot. For example, the vehicle may have integrated ultraviolet (UV) light sanitizing systems. After being sanitized appropriately, the pathogen detector may be run again to confirm pathogens are no longer detected (or the threshold amount of pathogens are no longer detected). A new vehicle health pass credential may then be requested. At any time, the passengers, fleet owners and drivers, and the vehicle itself may be able to verify the status of the vehicle by requesting and verifying the vehicle's health pass credential against Blockchain. In some cases, if the vehicle is not able clean itself on the spot, but rather needs to navigate to a cleaning facility, a second vehicle that is determined to satisfy the requisite cleanliness requirements may instead be assigned to the passenger and the initial vehicle may then be sent to the cleaning facility for cleaning for subsequent use by other passengers. Some or all of this information may be stored to the Blockchain to create an easily-accessible historical record of the status of the vehicles in the ride hail fleet, as well as any other information, such as passenger preferences, among other information.

Figure 8:
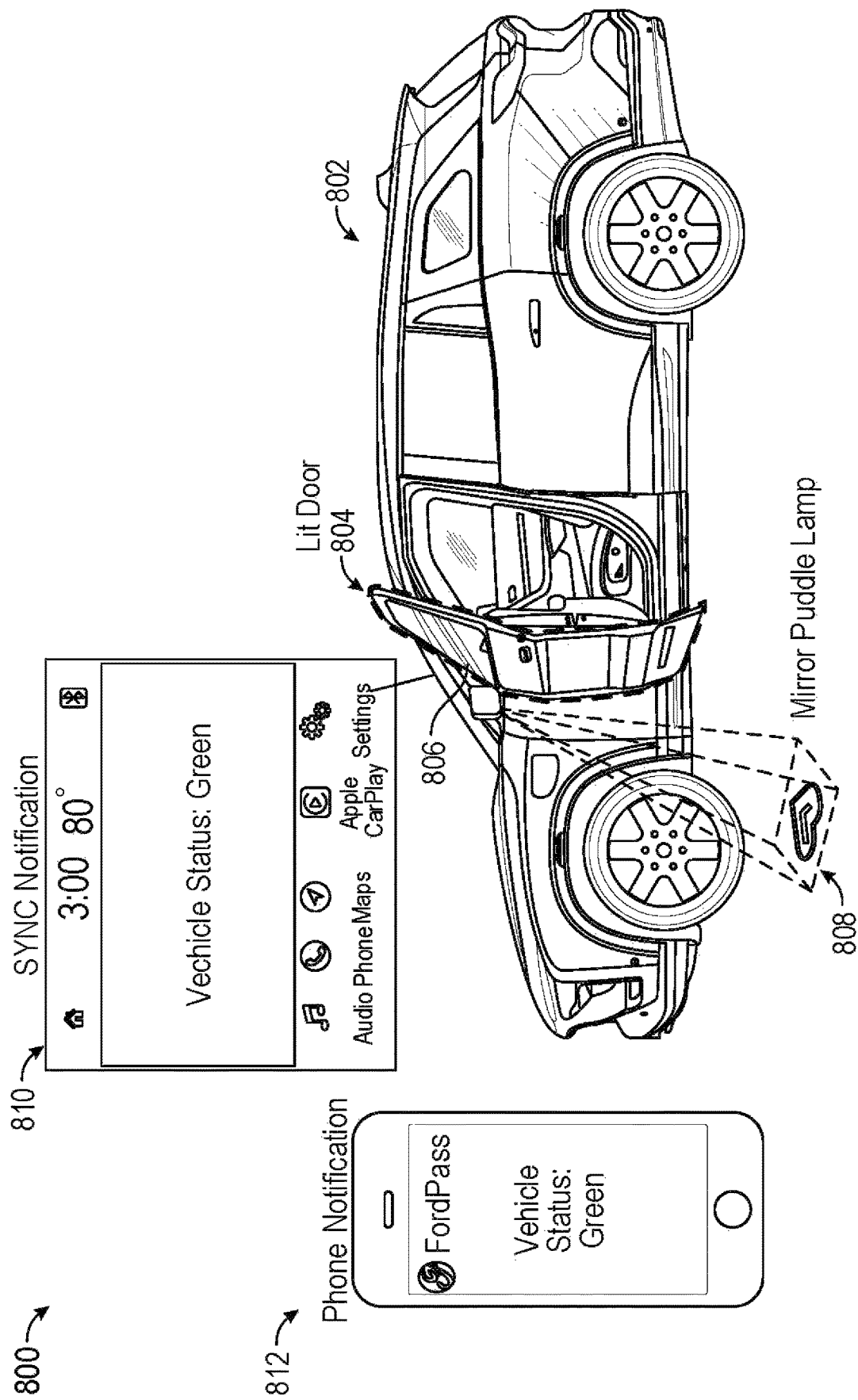
FIG. 8 illustrates an example system, in accordance with one or more embodiments of the disclosure.

In some cases, a status indicator may also be used to provide an indication of the status of the vehicle to a rider, driver, or any other user of the vehicle. For example, if it is determined that the pathogen detector identifies pathogens in the vehicle, a color of the status indicator may be changed to reflect the existence of the pathogens. As one example, the color may change to red. A status color of red may provide an indication that the vehicle needs to be sanitized and may be not ideal to use. When it is determined that the vehicle has been cleaned (for example, if the pathogen detector determines that the pathogens are no longer detected once the vehicle has been cleared), the status light may change to a different color. For example, the status light may change to a green color, which may indicate the vehicle is clean. In some case, the status light may be presented directly on or inside one or more parts of a vehicle. As depicted in FIG. 8, a door of the vehicle may include an associated status light that may be changed to different colors. As a second example, a puddle lamp may be projected from the vehicle. As a third example, the status may be presented on a human machine interface (HMI) of the vehicle. In some cases, the status light may be presented through the ride hail application presented on a mobile device of the user. Additional details about the status indicator may be depicted and described with respect to FIG. 8.

The systems and methods described herein may provide a number of advantages. As a first example, pathogen detection may be performed autonomously and automatically, increasing the speed at which pathogens are detected and reducing the opportunity for human error. Additionally, pathogen detection and vehicle cleaning are tracked on Blockchain, producing an immutable record of the vehicle's changing health status, increasing trust and confidence in the status of the vehicle. Passengers and drivers can use this vehicle information to make informed decisions whether to drive or enter vehicles in scenarios including daily driving, ride sharing, car rental, etc. Additional systems, like car rental or fleet management software can interface with the vehicle status to automate the assignment of vehicles based on their status. Clean vehicles can be approved for use, and vehicles needing further cleaning can be redirected for cleaning.

Turning to the figures, FIG. 1 illustrates an example flowchart 100, in accordance with one or more embodiments of the disclosure. The flowchart 100 may depict a high-level overview of operations performed in association with the systems and methods described herein. The flowchart 100 may begin with operations 104 and 104, which, in some cases, may be operations performed in association with a vehicle (such as a ride hail vehicle, for example). Operation 102 may involve collecting air quality data. The air quality data may be collected by a pathogen detection device. Once the air quality data is collected, the flowchart may proceed to condition 104. Condition 104 may involve a determination as to whether any pathogens are detected in the vehicle (for example, if any pathogens are detected by the pathogen detector device). If pathogens are detected in the vehicle, the flowchart 100 may proceed to operation 108. If no pathogens are detected in the vehicle, the flowchart 100 may proceed to operation 110. In some cases, the condition 104 may not necessarily involve a determination as to whether there are any pathogens in the vehicle, but may rather involve a determination as to whether a threshold amount of pathogens exist in the vehicle. This threshold amount may be a default amount that is applicable to all ride hail users, or may be a threshold amount that is based on an indicated preference of a particular user. Operations 108 and 110 may involve obtaining a vehicle health pass credential. From operation 108, the flowchart 100 may proceed to operation 112. Operation 112 may involve cleaning the vehicle. The cleaning may be performed through any suitable methods. In some cases, the vehicle may be equipped to perform the cleaning on the spot without having to traverse to a cleaning facility. For example, the vehicle may have integrated ultraviolet (UV) light sanitizing systems, thermal cleaning systems, and/or any other type of cleaning system. However, in some cases, the vehicle may not have such capabilities, and may be required to traverse to a designed cleaning facility. If the vehicle is an autonomous vehicle, the navigation system of the vehicle may automatically be altered in order to automatically route the vehicle to the cleaning facility. Additional details about the cleaning process itself may be provided in FIG. 6. From operation 110, the flowchart 100 may proceed to operation 114. Operation 114 may involve providing an indication that the vehicle is clean. For example, the indication may include a status indicator that may be presented on and/or inside the vehicle and/or on a mobile device of the user (for example, through a ride hail application). The status may also be provided in any other suitable manner as well. Following operations 112 and/or operation 114, the flowchart 100 may proceed to operation 116, which may involve repeating the cycle depicted in the flowchart 100. That is, the flowchart 100 may return to operation 102. In this manner, the system may iterate through operations 102-114 such that the vehicle may constantly or periodically be checked for pathogens and/or cleaned for customer use. In some cases, the vehicle may be checked for pathogens at certain predefined intervals, such as every time a ride hail passenger leaves a vehicle, or every time a ride hail vehicle is assigned to a passenger. As another example, a user may be able to manually set intervals at which the vehicle should be checked for pathogens. Software defined triggers (e.g. visiting a hospital or entering a geofenced area), may also be established to trigger the pathogen detection system as well. These are just examples of such intervals and are not intended to be limiting.

Figure 2:
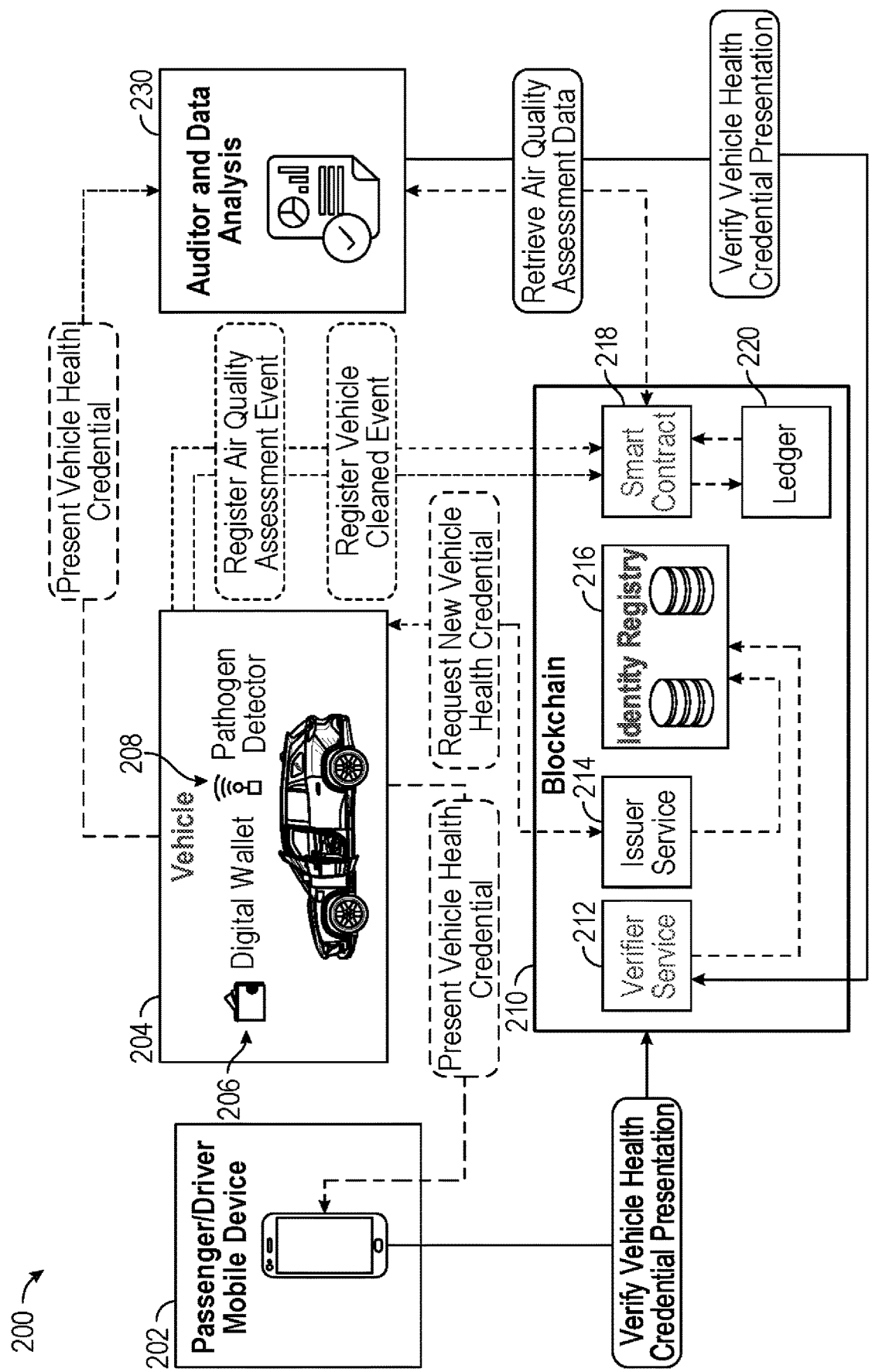
FIG. 2 illustrates an example system, in accordance with one or more embodiments of the disclosure.

FIG. 2 illustrates an example system 200, in accordance with one or more embodiments of the disclosure. In some embodiments, the system 200 may include at least a mobile device 202, a vehicle 204, a Blockchain 210, and/or an auditor and data analysis system 230. Additionally, it should be noted that any of these parts of the system 200 may include any of the elements of the machine 1000 described with respect to FIG. 10.

The mobile device 202 may include any type of user device, such as a smartphone, laptop computer, desktop computer, tablet, and/or any other type of mobile device. The mobile device may be capable of running an application. For example, the mobile device may include a ride hail application that may be used by a driver or passenger of a ride hail service. The application may allow a passenger to request a ride hail vehicle, request a vehicle cleanliness status, view a status of the vehicle, and/or perform any other operations with respect to the systems and methods described herein. The mobile device may also perform functions such as reading and verifying a vehicle health credential and/or presenting a verified vehicle health credential to a user through the application. In some cases, the mobile device may verify a vehicle health status that is stored on the Blockchain 210.

The vehicle 204 may include driverless autonomous vehicles and/or driver-operated vehicles. The vehicles may also include internal combustion engines (ICE), may be hybrid vehicles, or may be fully electric vehicles. The vehicles 204 may be vehicles included in a fleet of vehicles that may be rented by one or more rental customers (not depicted in the figure) through a ride hail service. The vehicle may also include a digital wallet 206 and/or a pathogen detector 208. The digital wallet 206 may refer to a storage mechanism by which any data associated with the Blockchain 210 may be stored at various portions of the system 200. For example, the mobile device 202 may have its own associated digital wallet 206 as well. In this manner, any of the portions of the system 200 may have access to the Blockchain 210 and the data included within the Blockchain 210. However, it should be noted that the mobile device 202 may not necessarily require a digital wallet in order to verify a vehicle health pas credential or perform other operations as described herein. The pathogen detector 208 may be a device integrated into the vehicle that may be used to determine if any pathogens exist in the vehicle.

The pathogen detector 208 may also be used to determine if a threshold number of pathogens exist in the vehicle 204. A pathogen detector may be a device that may be a standalone device or a device that is integrated into a vehicle. The pathogen detector may be capable of detecting bacterial and viral pathogens within a given environment, such as the interior of the vehicle. The pathogen detector may also be capable of transmitting collected data to a separate local or remote system for processing. The pathogen detector may be a direct air handling system for collecting airborne samples. The pathogen detector may include a biochip and/or a biosensor for detecting the presence of a pathogen. The pathogen detector may also include an integrated control module with embedded software. The pathogen detector may be housed within an integrated housing assembly for installation into vehicle interior cabin such as the center console. The air handling system may trap airborne pathogens within the vehicle and allow binding to a nanoprobe on a surface of the biochip. The biochip may then read optical characteristics of the biochip and output signals to the control module. The software in the control module may interpret the signals and output wireless data indicative of a level of pathogens found within the vehicle.

The pathogen detector 208 may be integrated with the vehicle 204 in a number of different ways. As a first example, the pathogen detector 208 may be integrated with an electric control unit (ECU) of the vehicle 204, which may place a signal on the CAN bus to be picked up by the gateway within the vehicle 204 that houses the on-vehicle wallet 206, keys, and Blockchain client. As a second example, the pathogen detector 208 may have an integrated Bluetooth chip (or other network transmission capabilities), which may transmit data to the vehicle 204 and may place data in the on-vehicle wallet 206. The vehicle 204 may also provide vehicle health credential presentation to the mobile device 202, provide an indication that an air quality assessment event has taken place to the Blockchain 210 for storage, provide an indication of a vehicle cleaning event to the Blockchain 210 for storage, and/or provide any other information tot eh Blockchain 210 for storage.

The auditor and data analysis system 230 may be third-party agencies (e.g., government or non-profit) which would assess in-vehicle air quality for fleets. The auditor and data analysis system 230 may also read and verify the vehicle health credential presentations from the vehicle 204, and read and analyze air quality assessment data from the Blockchain 210.

The Blockchain 210 may be a form of a distributed ledger technology, for example, which may be an immutable, sequential record of transactions on, or changes in the state of, a specific item of value over a geographically disperse computer network without using a central authority. For example, data relating to the cleanliness status of various vehicles 204 in a ride hail fleet may be managed through a distributed ledger, providing the entire transaction history, state changes, and life cycle of a the vehicle before, during, and after the lifetime of one or more rentals of the vehicle. In this way, the Blockchain 210 acts like a biography of the vehicle 204. The use of the distributed ledger system may provide a secure method for data analysis and storage. This may be because the decision to add a transaction to the ledger may be made by consensus of the nodes in the distributed ledger system (for example, a consensus may refer to a majority of nodes determining that the transaction to be added is a valid transaction). The use of the ledger system may allow this information to be secured by default, but may also allow the owner to intervene and either access the data or perform remote functions associated with the vehicle if certain triggering conditions are met.

The Blockchain 210 may include a verifier service 212, an issuer service 214, a registry 216, a smart contract 218, and/or a ledger 220. The verifier service 212 may include systems used to verify the authenticity of credentials issued in association with the ride hail services as described herein. The issuer service 214 may issue credentials, whose record of issuance is stored on Blockchain 210. The issuer service 214 may be able to consume various values needed in order to issue a credential. The registry 216 may be a decentralized ledger that may store the identities of issuers and credential schemas for all credentials, and may allow verifiers to confirm the authenticity of credentials that are presented to them. The issuer service 214 may create and digitally sign credentials that holders may obtain and save. Credentials are issued to the subject (e.g., the vehicle) directly using a privacy preserving bi-lateral connection (e.g., API) between the issuer and the subject. The credentials can include private data attributes. This method may ensure that no private data is stored on the ledger, but rather as verifiable credentials on the vehicle itself. The verifier service 212 may not require any connection to the issuer service 214. The verifier service 212 may obtain the verifiable presentation from the subject and validate it against the ledger 220. The smart contract 218 may refer to a system associated with Blockchain that runs when predetermined conditions are met. The smart contract 218 may be used to automate the execution of an agreement so that all participants can be immediately certain of the outcome, without any intermediary's involvement or time loss. Finally, the ledger 220 may be a decentralized and distributed information source that may be continuously updated, distributed, and/or stored at other parts of the system 200. Some or all nodes of the one or more nodes may also have access to and/or have stored the same or a similar ledger 220. This may allow the nodes to be apprised of the same ledger information (data relating to the cleanliness status of various vehicles in the ride hail fleet) at any given time. Updating the ledger 220 can thus include, for example, adding a block of data corresponding to the ledger record. To reduce the amount of information saved at the ledger 220 and thus reduce the storage requirements of each of the nodes, information may also be stored remotely from the ledger 220. That is, the ledger 220 may simply include pointers to such "off-chain" information.

In some embodiments, a vehicle health pass credential may be a digital certificate issued to the vehicle using the W3C Verifiable Credentials standard, for example. To that end, the vehicle may have its own Blockchain-based Self-Sovereign Identity (SSI) using the W3C Decentralized Identifier (DID) standard. In the DID ecosystem, verifiable credentials can be issued by anyone, about anything, and can be presented to and verified by everyone. In case of the vehicle health pass credential use-case, the verifiable credential may be issued to the vehicle, which may be the holder that stores it for later use. The credential may be issued by the OEM or a trusted third-party, which may be the issuer. Verifiable credentials may be digitally signed by the issuer, which may make them tamper-resistant and instantaneously verifiable, allowing the holder to prove something about themselves (e.g., in-vehicle air quality status) by presenting their credentials to a verifier (e.g. the rider). The vehicle health pass credential may be associated with different types of information. For example, the vehicle health pass credential may include information such as an ID, a date, a vehicle ID, an air quality system ID, a biochip ID, a location, a pathogen detection indication, a type of pathogen, a cleaning indication, a cleaning type, a safety indication and/or any other types of information. The ID may refer to a public key or decentralized identifier (DID) of a holder system, for example, in this case the vehicle 204. The date may refer to date of a pathogen detection scan performed in the vehicle 204 by the pathogen detector 206. The vehicle ID may include a unique ID of the vehicle 204 (for example, a VIN number of the vehicle or any other identifier). The air quality system ID may include an identifier associated of the air quality monitoring system (for example, an identifier for the pathogen detector 206). The biochip ID may be an ID associated with a biochip used in the scan (for example, a biochip included with the pathogen detector 206). The location may refer to a location of the vehicle at time of the scan. The pathogen detection indication may provide an indication as to whether pathogens were detected and/or a threshold number of pathogens were detected. Possible values for the pathogen detection indication may include Boolean values, such as true and/or false. However, values may include any other types of indications as well. The type of pathogen may include a name of pathogen detected. The cleaning indication may be an indicator as to whether the vehicle has been cleaned. Possible values for the pathogen detection indication may include Boolean values, such as true and/or false. However, values may include any other types of indications as well. The cleaning type may refer to a type of sanitization used to clean the vehicle (for example, UV light, chemical cleaning, thermal cleaning, etc.). Possible values for the pathogen detection indication may include Boolean values, such as true and/or false. However, values may include any other types of indications as well.

In some embodiments, a smart contract 218 may also be associated with certain types of information. For example, the smart contract 218 may include air quality assessment data, vehicle data, cleaning record data, all air quality assessments data, all cleanings data, vehicles data, assessments data, cleanings data, pathogens detected data, no pathogens detected data, air quality assessed non-ideal data, vehicle cleaned data, and/or any other types of data.

The air quality assessment data may include data collected each time an air quality assessment is performed. The air quality assessment data may include date, time, vehicle ID, and/or pathogen detected data, as well as any other types of data. Date may refer to a date of air quality assessment date of air quality assessment. Time may refer to a time of air quality assessment. Vehicle ID may refer to an ID of vehicle where assessment occurred. The pathogen detection indication may provide an indication as to whether pathogens were detected and/or a threshold number of pathogens were detected. Possible values for the pathogen detection indication may include Boolean values, such as true and/or false. However, values may include any other types of indications as well.

The vehicle data may include air quality assessment data for an individual vehicle. The vehicle data may include pathogens detected, assessments, clear of pathogens, clean, and/or any other types of data. Pathogens detected may refer to total assessments when pathogens were detected. No pathogens detected may refer to total assessments when pathogens were not detected. Assessments may refer to total number of air quality assessments. Clear of pathogens may refer to indicator if there are no pathogens currently detected. Clean may refer to indicator if the vehicle is currently clean.

The cleaning record may include records collected each time the vehicle is cleaned. The cleaning record may include cleaning type, date, time, and/or any other types of data. Cleaning type may refer to type of cleaning used. Date may refer to date of cleaning date of air quality assessment. Time may refer to a time of cleaning. In some cases, cleaning records may include a specific air quality assessment based on the assessment number, all air quality assessments that have ever been performed, all air quality assessments for a specific vehicle, all vehicles that are clean (for example, all vehicles that are clear of pathogens and have been cleaned), and/or any other types of information.

The smart contract 218 may also include other types of data. For example, the smart contract 218 may include all air quality assessments data, all cleanings data, vehicles data, assessments data, cleanings data, pathogens detected data, no pathogens detected data, air quality assessed non-ideal data, vehicle cleaned data, and/or any other types of data. All air quality assessments may include mapping of all air quality assessments. All cleanings may include mapping of all cleaning records. Vehicles may include mapping of all vehicles. Assessments may include total number of air quality assessment performed. Cleanings may include total number of cleanings. Pathogens detected may include total number of assessments where pathogens were detected. No pathogens detected may include total number of assessments where no pathogens were detected. Air quality assessed clean may include event representing an assessment where no pathogens were detected. Air quality assessed as not ideal may include event representing an assessment where pathogens were detected. Vehicle cleaned may include event representing the vehicle was cleaned.

Figure 3A:
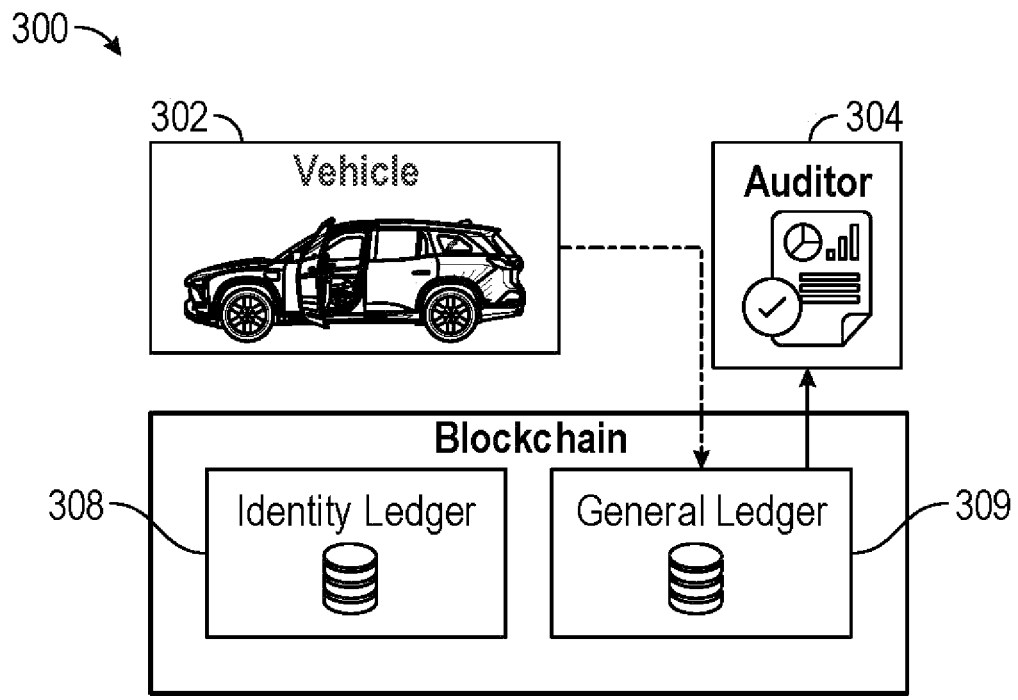
FIGS. 3A-3C illustrate example Blockchain architectures, in accordance with one or more embodiments of the disclosure.
Figure 3B:
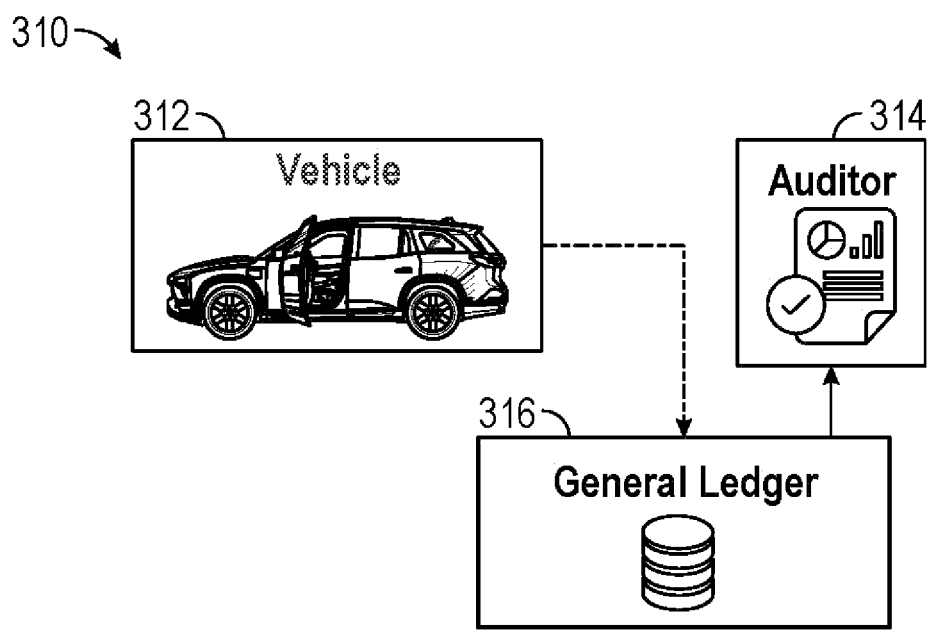
Figure 3C:
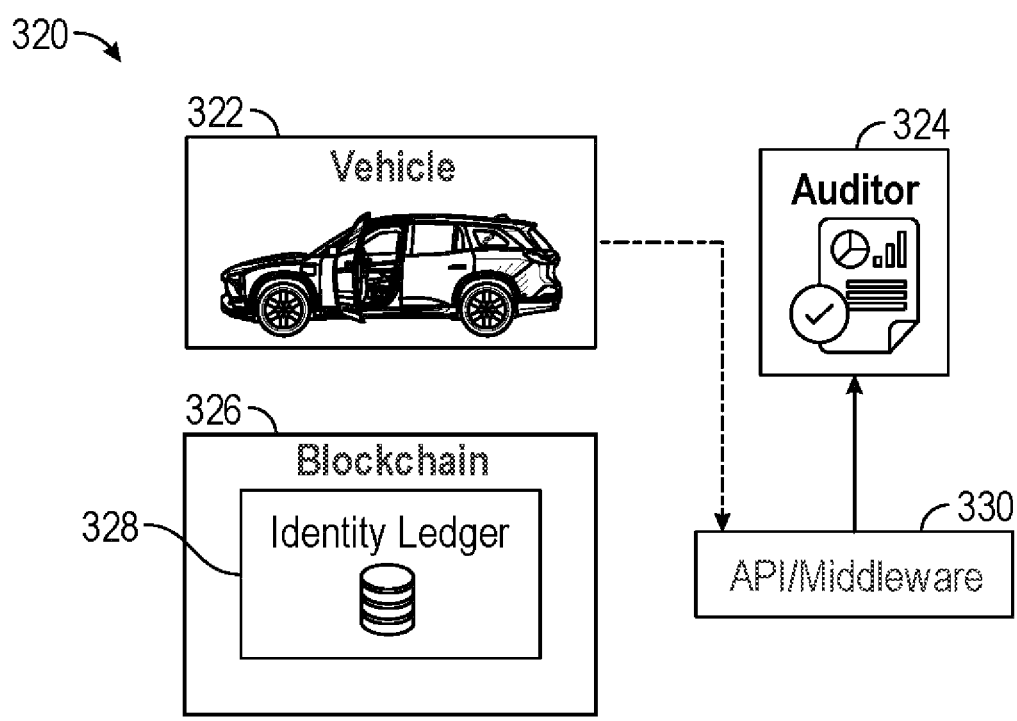

FIGS. 3A-3C illustrate example Blockchain architectures, in accordance with one or more embodiments of the disclosure. FIGS. 3A-3C illustrate that various approaches to the Blockchain architecture may be applied to the systems and methods described herein. FIG. 3A illustrates a first architecture 300. The first architecture 300 may use an identity ledger 308 (e.g., Hyperledger Indy) to handle credential requests and a general-purpose ledger 309 (e.g., Hyperledger Fabric) to handle solution logic. FIG. 3B illustrates a second architecture 310. The second architecture 310 may use a single general-purpose ledger capable of partitioning data, e.g. multiple chaincodes and channels on a platform such as Hyperledger Fabric, 316 to handle both credential requests and solution logic. FIG. 3C illustrates a third architecture 320. The third architecture 320 may use an identity ledger 328 to handle credential requests and a centralized solution 330 (e.g., a middleware with a relational or non-structured database) to handle solution logic. Using a single general-purpose ledger may generally be more cost effective from an operational standpoint, whereas dividing up the architecture into multiple ledgers may prove more robust and easier to operate.

Figure 4:
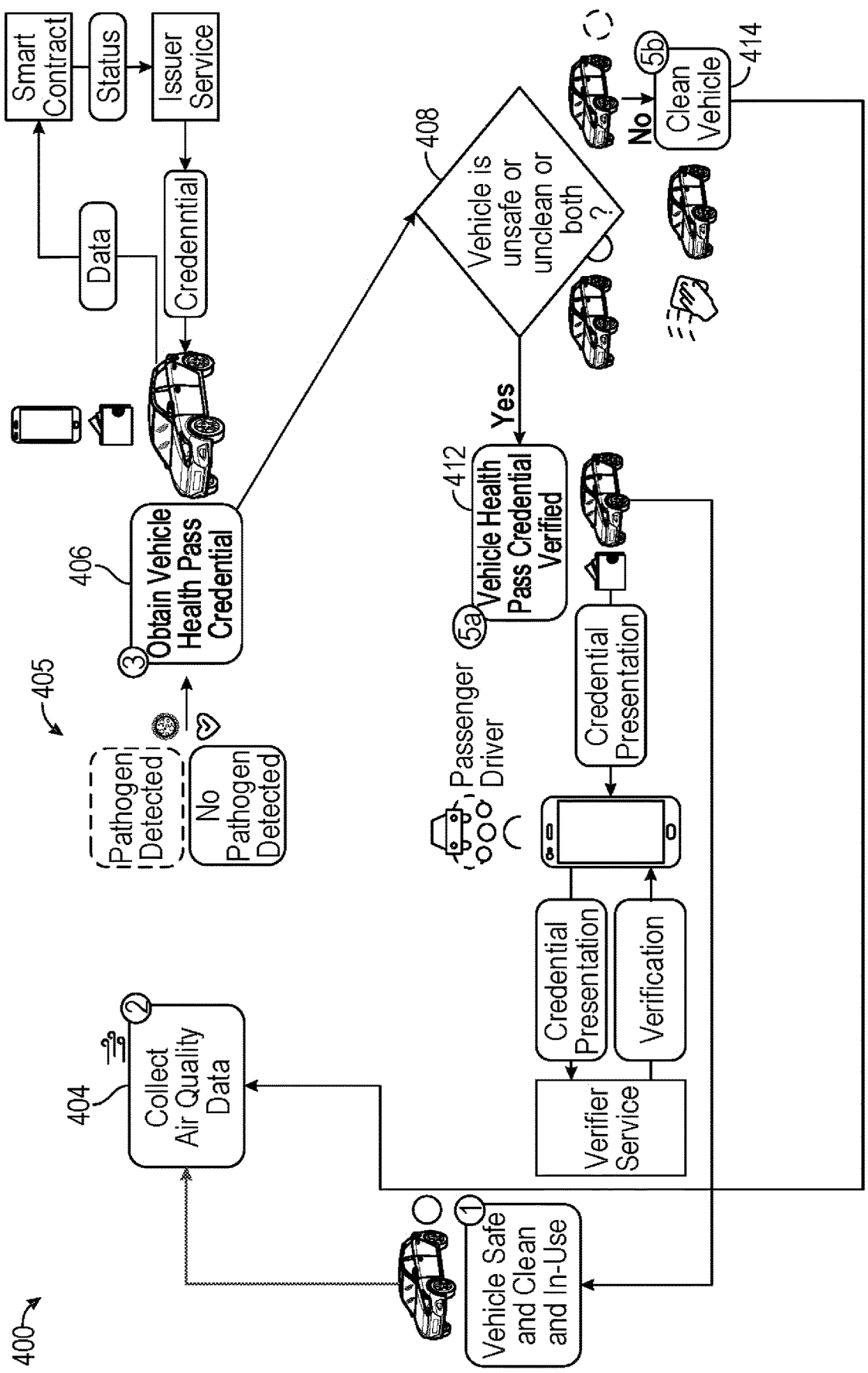
FIG. 4 illustrates an example flowchart, in accordance with one or more embodiments of the disclosure.

FIG. 4 illustrates an example flowchart 400, in accordance with one or more embodiments of the disclosure. The flowchart 400 may be a more detailed version of the flowchart 100 depicted in FIG. 1. The flowchart 400 may begin at operation 402 with the vehicle being clean, and in-use (for example, in-use by a ride hail passenger). Following operation 402, the flowchart 400 may proceed to operation 404. Operation 404 may involve collecting air quality data from the vehicle. The air quality data may be collected by a pathogen detection device. Following operation 404, operation 405 may involve determining whether any pathogens are detected in the vehicle. Alternatively, operation 405 may involve determining whether a threshold number of pathogens are detected in the vehicle. The pathogen detector device may be integrated with the vehicle in a number of different ways. As a first example, the pathogen detector device may be integrated with an electric control unit (ECU) of the vehicle, which may place a signal on the CAN bus to be picked up by the gateway within the vehicle that houses the on-vehicle wallet, keys, and Blockchain client. As a second example, the pathogen detector device may have an integrated Bluetooth chip (or other network transmission capabilities), which may transmit data to the vehicle and may place data in the on-vehicle wallet. Following operation 405, operation 406 may involve obtaining a vehicle health pass credential. In some cases, the data from the pathogen detector may be sent from the vehicle to a smart contract of the Blockchain, which may process the data, determine a status of the vehicle, store the data and the status, and forward the information to an issuer-service of the Blockchain. The issuer service may then return a vehicle health pass credential to the vehicle. This credential may then be stored in the on-vehicle wallet. Additionally, any of the information produced from any of the operations described herein may be stored on the Blockchain in order to provide a comprehensive history relating to the status of various vehicles included in a ride hail fleet.

Following operation 406, the flowchart 400 may proceed to condition 408. Condition 408 may involve a determination as to whether the vehicle is sufficiently clean for a ride hail passenger. This determination may involve using the pathogen detector to determine if any pathogens are detected in the vehicle (and/or if a threshold amount of pathogens are detected in the vehicle). If it is determined that the vehicle is not sufficiently clean, then the flowchart 400 may proceed to operation 414. If it is determined that the vehicle is sufficiently clean, then the flowchart 400 may proceed to operation 412. Operation 414 may involve cleaning the vehicle. The vehicle may be cleaned using any number of suitable methods. For example, the vehicle may be cleaned using chemical solutions. As a second example, the vehicle may be cleaned using ultraviolet (UV) sanitation. The vehicle may also be cleaned using any other method. In some cases, the vehicle may be equipped to perform the cleaning on the spot without having to traverse to a cleaning facility. For example, the vehicle may have integrated ultraviolet (UV) light sanitizing systems. However, in some cases, the vehicle may not have such capabilities, and may be required to traverse to a designed cleaning facility. If the vehicle is an autonomous vehicle, the navigation system of the vehicle may automatically be altered in order to automatically route the vehicle to the cleaning facility. Operation 412 may involve verifying the vehicle health pass credential. Prior to accessing the vehicle, any passengers and/or drivers may verify the credential and confirm the status of the vehicle. The credential is requested from the the vehicle wallet. The credential may then be presented on an HMI of the vehicle, through an application of the user mobile device, or in any other manner. As described with respect to FIG. 8, a status indicator in the form of a color light may also be presented on or in the vehicle or through the application of the user mobile device. Following operations 412 and/or 414, the flowchart 400 may proceed back to operation 404. In the case that the vehicle needed to be cleaned, the system may then collect additional air quality data to determine if the cleaning performed in operation 414 was sufficient. That is, the pathogen detector of the vehicle may again check the vehicle to determine if any pathogens exist within the vehicle (and/or if a threshold number of pathogens exist in the vehicle). The system may also continue to check the vehicle for pathogens constantly or periodically. For example, the vehicle may perform a check upon every request for a ride hail service from a user, at certain pre-defined time intervals, every time a ride hail rider exists a vehicle, at a request by a user, or at another interval.

Figure 5:
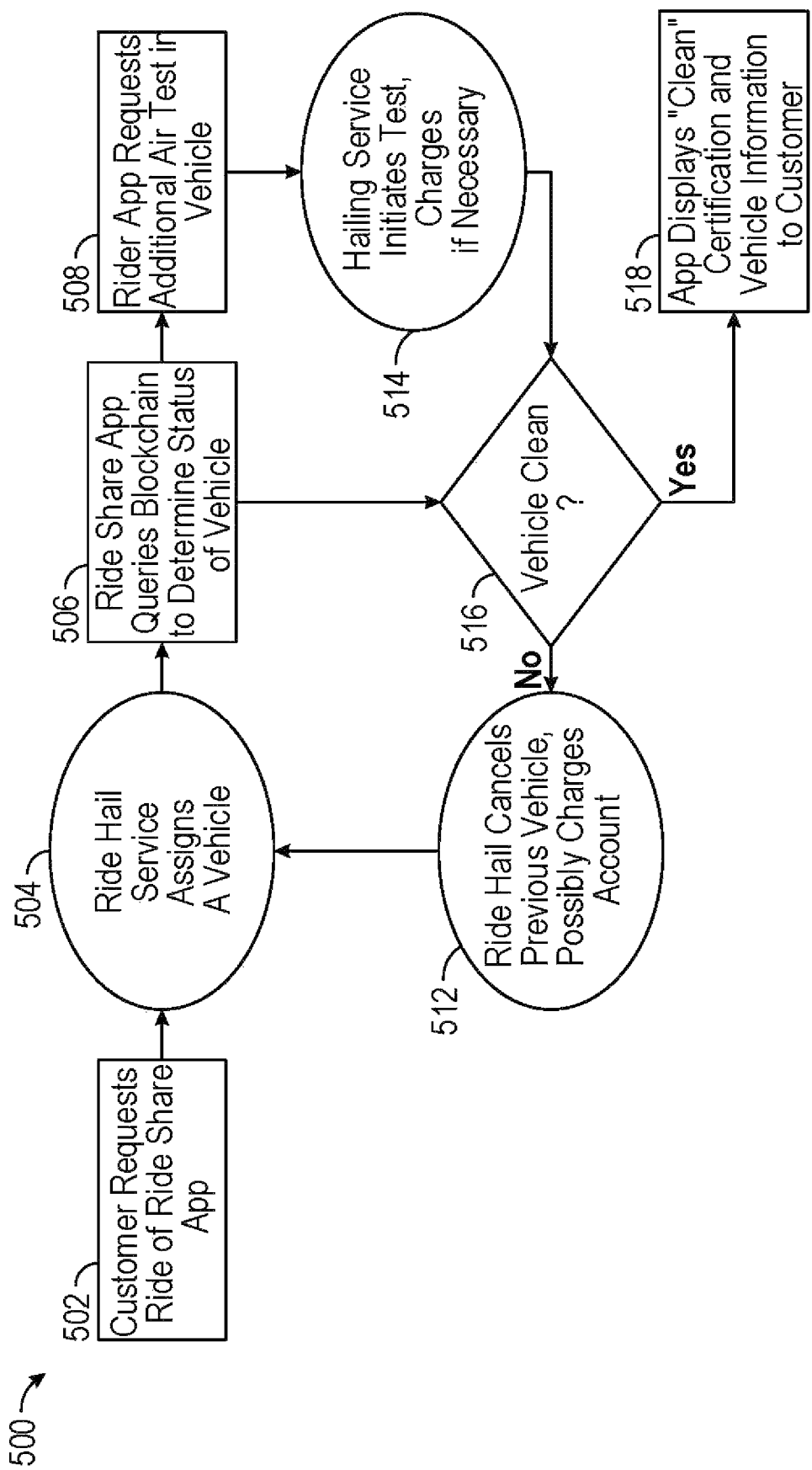
FIG. 5 illustrates an example flowchart, in accordance with one or more embodiments of the disclosure.

FIG. 5 illustrates an example flowchart 500, in accordance with one or more embodiments of the disclosure. The flowchart 500 may illustrate a logical flow involving a determination if a vehicle is clean and ready for a ride hail passenger (for example, by a ride hail application of the user's mobile device). In some cases, this may allow the ride hail user (or user's organization) to set their own preferences as to what constitutes a sufficiently clean vehicle for use by the user. The flowchart 500 may also account for charging a user account for performing a cleanliness test on a first assigned vehicle or cancelling the initially-assigned vehicle and re-requesting another vehicle. The flowchart 500 may begin with operation 502, which may involve requesting a ride from a ride hail application of a user. Following operation 502, operation 504 may involve a vehicle being assigned to the user by a ride hail service based on the request. Following operation 504, operation 506 may involve the ride hail application querying the Blockchain to determine a status of the vehicle. As described herein, a status of the vehicle may refer to a cleanliness state of the vehicle. For example, the vehicles included in the ride hail fleet may be equipped with pathogen detectors that may be used to determine if any pathogens exist in a given ride hail vehicle. Following operation 506, operation 508 may involve receiving a request from the ride hail application for an additional air test in the vehicle. For example, the user may indicate through their ride hail application that they desire for the vehicle assigned to them to be tested for pathogens. Following operation 508, Operation 514 may involve the ride hail service initiating a test in the vehicle. For example, the pathogen detector integrated within the vehicle may test the vehicle to determine if any pathogens exist in the vehicle. In some cases, the pathogen detector may test to determine if a threshold number of pathogens exist in the vehicle. In some cases, the threshold number may be based on a user preference. For example, the user may pre-establish settings through the ride hail application as to the threshold level of pathogens that is acceptable for an assigned ride hail vehicle. Following operation 514, the flowchart may proceed to condition 516. Condition 516 may involve a determination as to whether the vehicle is clean. For example, the condition may be based on whether any pathogens are detected in the vehicle and/or if a given threshold amount of pathogens are detected in the vehicle. If it is determined the vehicle is clean, then the flowchart 500 may proceed to operation 518. Operation 518 may involve the application displaying an indication of a "clean" certification and vehicle information to the customer. If, however, it is determined that the vehicle is not clean, the flowchart 500 may proceed to operation 512. Operation 512 may involve cancelling the previously-assigned vehicle. In such cases, the ride hail application may automatically request a new vehicle and/or the ride hail service may automatically assign a new vehicle to the user. Additionally, the ride hail service may optionally identify a vehicle that satisfies the cleanliness requirements of the user such that the user may not need to request a second test for the newly-assigned vehicle. Additionally, in some cases, the cleanliness test may automatically be performed even before it is required by a user. The test may automatically be performed based on preferences of the user or based on default pathogen thresholds that may apply to all ride hail users.

Figure 6:
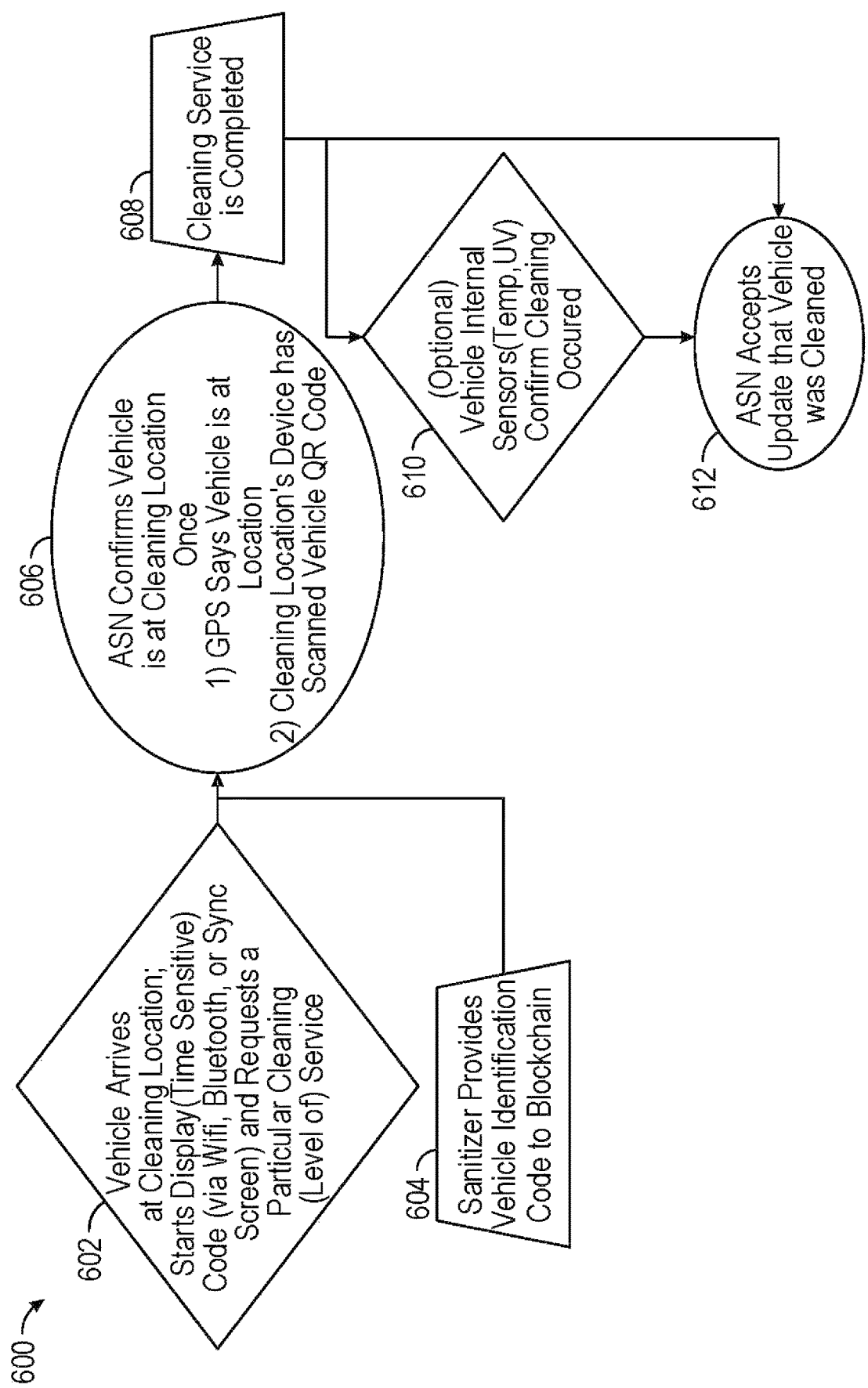
FIG. 6 illustrates an example flowchart, in accordance with one or more embodiments of the disclosure.

FIG. 6 illustrates an example flowchart 600, in accordance with one or more embodiments of the disclosure. The flowchart 600 may present a logical flow that may be used to add assurances that a vehicle is actually cleaned when a cleaning request is made by a user. That is, the flowchart 600 may present operations that may be performed once a user has actually initiated a request for a vehicle cleaning (and/or when a vehicle cleaning is automatically scheduled without a request from a user). The flowchart 600 may begin with operation 602. Operation 602 may involve a vehicle arriving at a cleaning location. Operation 602 may also involve a vehicle displaying a code and requesting a particular type of cleaning service. The code may be a time-sensitive code in some cases. The code may be presented wirelessly (for example, via WiFi, Bluetooth, or any other wireless methods) or may be presented visually (for example, through the HMI of the vehicle or through any other part of the vehicle). In some cases, the code may be a QR code, however, the code may also be in any other form. Operation 604 may involve the vehicle identification code being provided to the Blockchain. Operation 606 may involve the smart contract confirming the vehicle is at the cleaning location. This confirmation may be performed in any number of suitable manners. For example, the location confirmation may include using GPS within the vehicle to determine that the vehicle is at the location. Another example may include a determination that a device at the cleaning location has scanned the vehicle code. Operation 608 may be followed by condition 610. Condition 610 may include a determination as to whether the cleaning has occurred at the cleaning location. In some cases, this determination may be performed by the pathogen detector integrated into the vehicle. In some cases, the determination may also be determined using any other vehicle sensors (for example, a camera, etc.). If so, the flowchart 600 may proceed to operation 612. Operation 612 may involve the smart contract accepting an update that the vehicle was cleaned.

Figure 7:
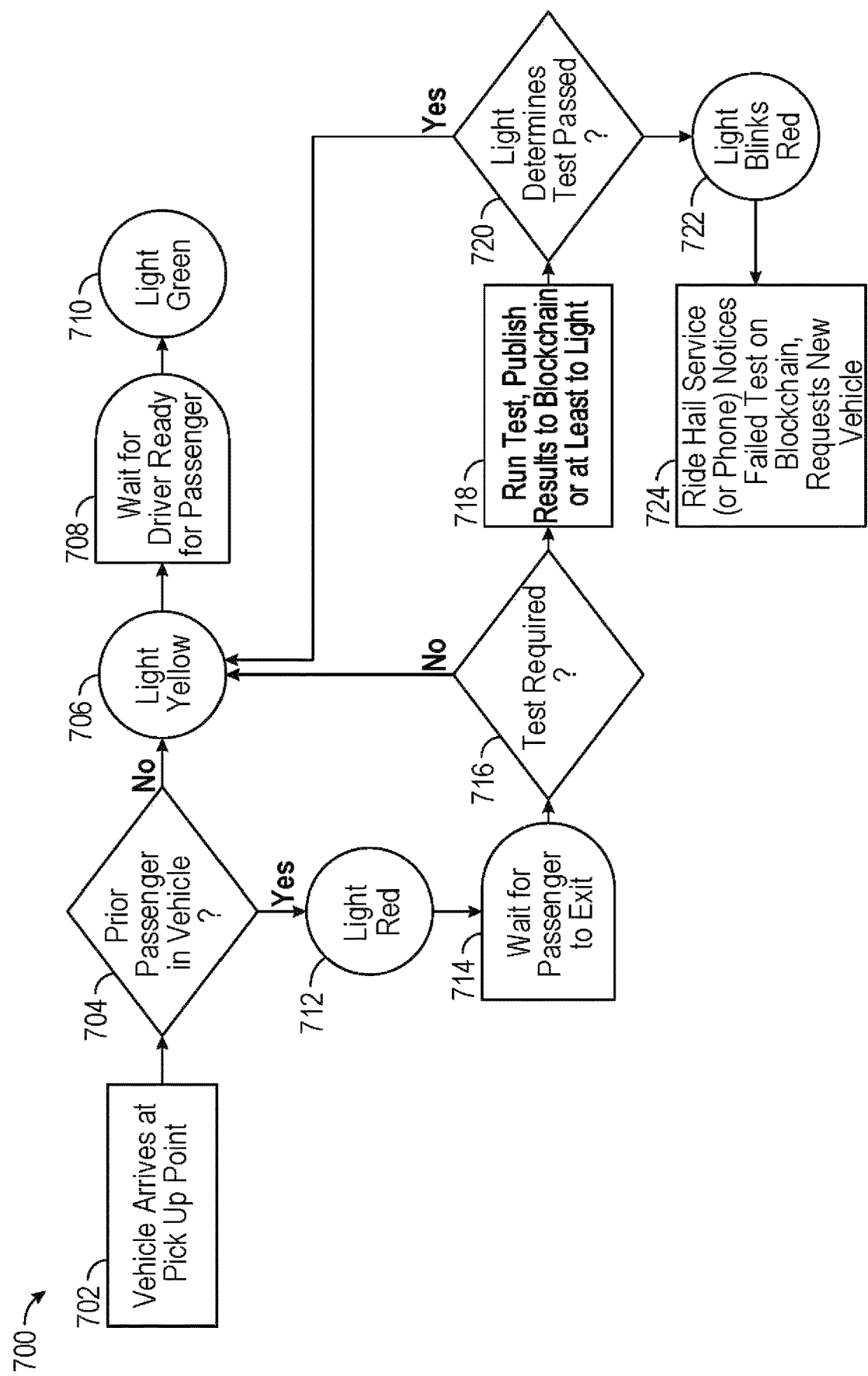
FIG. 7 illustrates an example flowchart, in accordance with one or more embodiments of the disclosure.

FIG. 7 illustrates an example flowchart 700, in accordance with one or more embodiments of the disclosure. The flowchart 700 may present a logical flow for when different status indicators may be presented to a user. In addition to, or as an alternative to an in-app notification, a status light built into the vehicle can confirm a readiness of the vehicle for the user. Used in conjunction with the application and Blockchain, this may provide faster final confirmation a vehicle is ready (e.g., if user doesn't have internet connectivity at point of pickup, or there is a brief period—perhaps a test is running after the prior passenger exists—where the vehicle should not be entered). To boost confidence in the system, the status indicator can operate using its own logic and have its own connection to the Blockchain. To maintain user preferences, the status indicator could have multiple operating modes for sensitivity or required test frequency (for example, every ride, every fifth ride, etc.) and could register those preferences before pickup when ride is accepted. In some cases, the status indicator may be in the form of a color light that may change colors to represent different statuses of the vehicle. However, the status indicator may be presented in any other form, such as an auditory indicator, or another type of visual indication, for example.

The flowchart 700 may begin with operation 702, which may involve determining that the vehicle has arrived at a pick-up point. The pick-up point may refer to a pick-up location requested by a user requesting a ride hail ride. Operation 702 may be followed by condition 704, which may involve a determination as to whether there a prior passenger that is still seated within the vehicle. If condition 704 is met, the flowchart may proceed to operation 712. If condition 704 is not met, the flowchart 700 may proceed to operation 706. Operation 706 may involve changing a color of the status indicator on the vehicle to yellow. Operation 706 may be followed by operation 708, which may involve waiting for the driver to indicate that they are ready for the passenger to enter the vehicle. Operation 708 may be followed by operation 710, which may involve the status indicator of the vehicle changing to a green color.

Operation 712 may involve the status light of the vehicle being displayed as red. Operation 712 may be followed by operation 714, which may involve waiting for the current passenger to exit the vehicle. Operation 714 may be followed by condition 716, which may involve a determination as to whether a test is required. If it is determined that a test is not required, the flowchart 700 may proceed to operation 706. If it is determined that the test is required, the flowchart 700 may proceed to operation 718. Operation 718 may involve running the test and publishing the results to the Blockchain. Operation 718 may be followed by condition 720. Condition 720 may involve a determination as to whether the test is passed. If the condition is met, then the flowchart 700 may proceed to operation 706. If the condition 720 is not met, then the flowchart 700 may proceed to operation 722. Operation 722 may involve the status light of the vehicle blinking red. Operation 722 may be followed by operation 724, which may involve the ride hail service requesting a new vehicle. This may be based on identifying the failed test on the Blockchain.

FIG. 8 illustrates an example system 800, in accordance with one or more embodiments of the disclosure. In some cases, the system 800 illustrated in FIG. 8 may provide examples of different methods by which a status of a vehicle 802 may be presented to a user. For example, as indicated in the flowchart 700 of FIG. 7, different color status indicators may be presented to a user based on the cleanliness status of the vehicle (or based on any other relevant information associated with the vehicle). In some case, the status light may be presented directly on or inside one or more parts of a vehicle 802. As depicted in the figure, a door 804 of the vehicle may include an associated status light 806 that may be changed to different colors. As a second example, a puddle lamp 808 may be projected from the vehicle 802. As a third example, the status may be presented on an HMI 810 of the vehicle 802. This status can either directly come from Blockchain, or alternately, the vehicle's health pass credential could be presented via a QR code displayed on the vehicle HMI, that the user can scan and verify against Blockchain. In some cases, the status light may be presented through the ride hail application presented on a mobile device 812 of the user.

Figure 9:
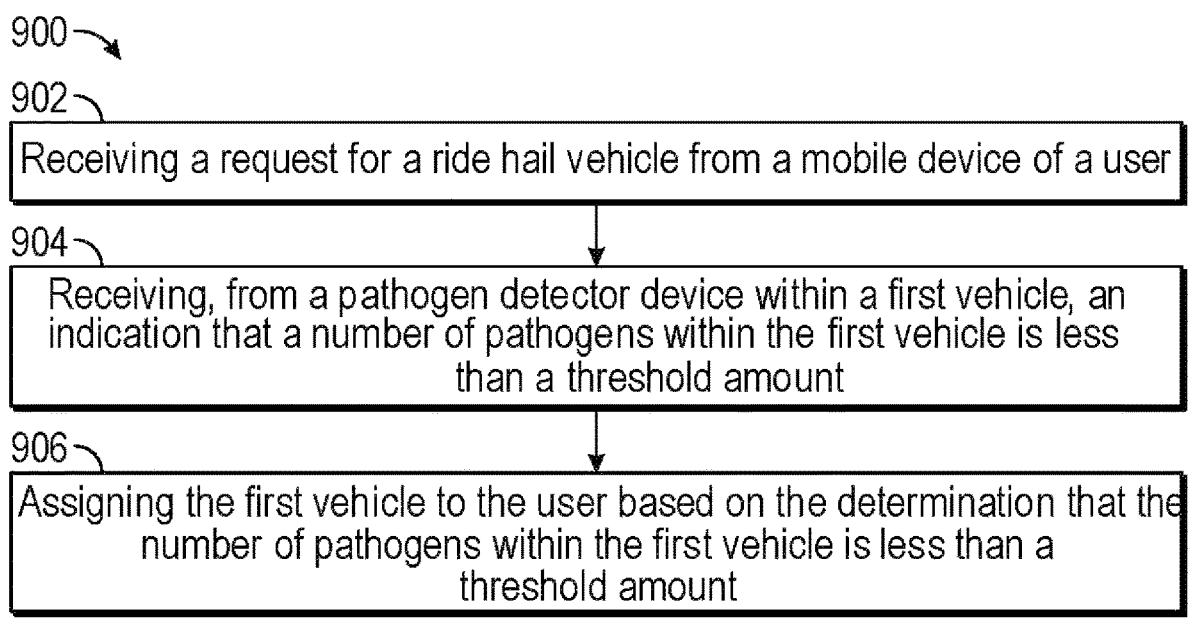
FIG. 9 illustrates an example method, in accordance with one or more embodiments of this disclosure.

FIG. 9 illustrates an example method 900, in accordance with one or more embodiments of this disclosure. At block 902, the method 900 may include receiving a request for a ride hail vehicle from a mobile device of a user. At block 904, the method 900 may include receiving, from a pathogen detector device within a first vehicle, an indication that a number of pathogens within the first vehicle is less than a threshold amount. Block 906 of the method 900 may include assigning the first vehicle to the user based on the indication that the number of pathogens within the first vehicle is less than a threshold amount.

Figure 10:
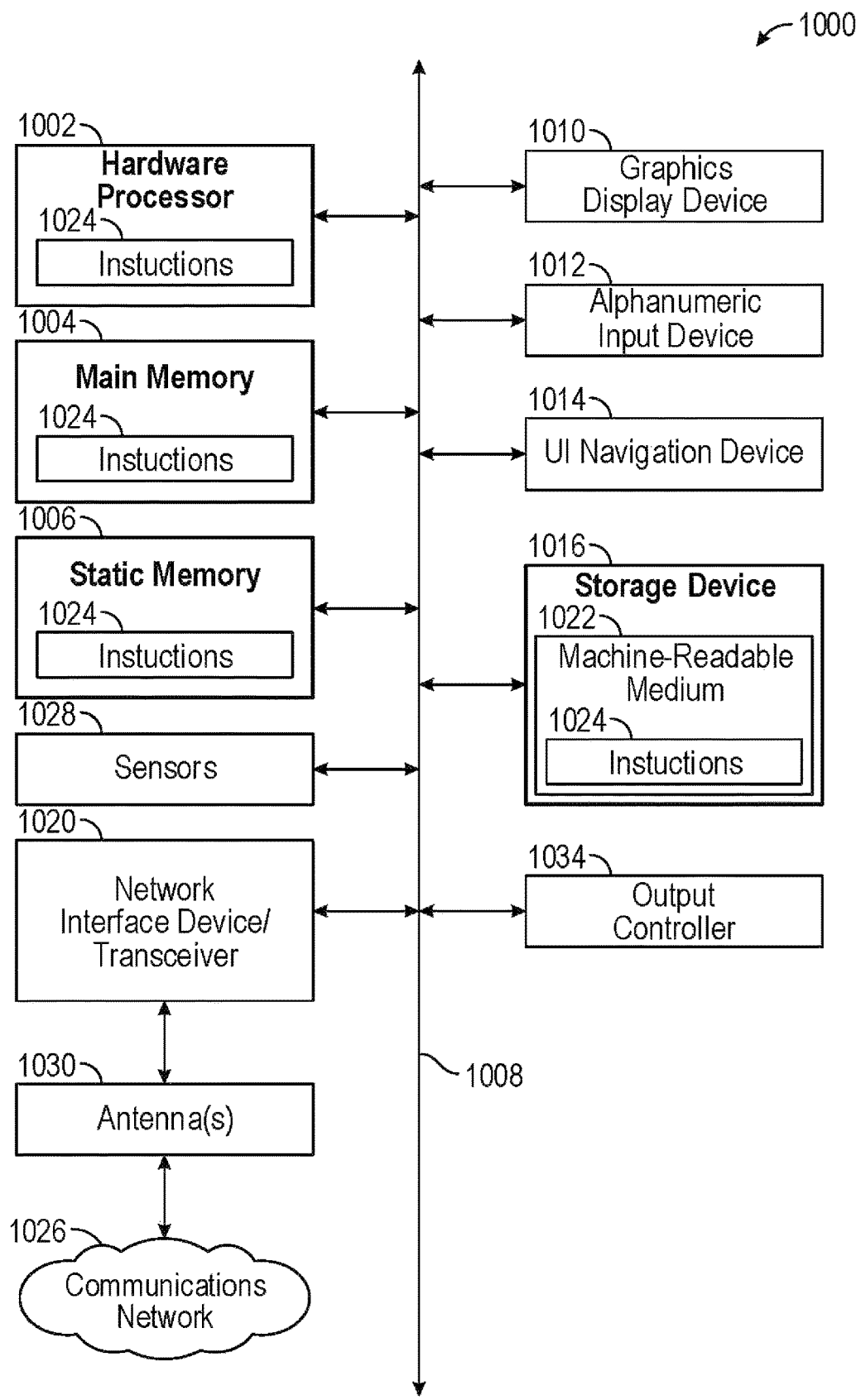
FIG. 10 illustrates an example of a computing system, in accordance with one or more embodiments of this disclosure.

FIG. 10 depicts a block diagram of an example machine 1000 upon which any of one or more techniques (e.g., methods) may be performed, in accordance with one or more example embodiments of the present disclosure. In other embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environments. The machine 1000 may be a personal computer (PC), a tablet PC, a set-top box (STB), a personal digital assistant (PDA), a mobile telephone, a wearable computer device, a web appliance, a network router, a switch or bridge, or any machine capable of executing instructions (sequential or otherwise) that specify actions to be taken by that machine, such as a base station. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), or other computer cluster configurations.

Examples, as described herein, may include or may operate on logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer readable medium containing instructions where the instructions configure the execution units to carry out a specific operation when in operation. The configuring may occur under the direction of the executions units or a loading mechanism. Accordingly, the execution units are communicatively coupled to the computer-readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

The machine (e.g., computer system) 1000 may include a hardware processor 1002 (e.g., a central processing unit (CPU), a graphics processing unit (GPU), a hardware processor core, or any combination thereof), a main memory 1004 and a static memory 1006, some or all of which may communicate with each other via an interlink (e.g., bus) 1008. The machine 1000 may further include a graphics display device 1010, an alphanumeric input device 1012 (e.g., a keyboard), and a user interface (UI) navigation device 1014 (e.g., a mouse). In an example, the graphics display device 1010, alphanumeric input device 1012, and UI navigation device 1014 may be a touch screen display. The machine 1000 may additionally include a storage device (i.e., drive unit) 1016, a network interface device/transceiver 1020 coupled to antenna(s) 1030, and one or more sensors 1028, such as a global positioning system (GPS) sensor, a compass, an accelerometer, or other sensor. The machine 1000 may include an output controller 1034, such as a serial (e.g., universal serial bus (USB), parallel, or other wired or wireless (e.g., infrared (IR), near field communication (NFC), etc.) connection to communicate with or control one or more peripheral devices (e.g., a printer, a card reader, etc.)).

The storage device 1016 may include a machine readable medium 1022 on which is stored one or more sets of data structures or instructions 1024 (e.g., software) embodying or utilized by any one or more of the techniques or functions described herein. The instructions 1024 may also reside, completely or at least partially, within the main memory 1004, within the static memory 1006, or within the hardware processor 1002 during execution thereof by the machine 1000. In an example, one or any combination of the hardware processor 1002, the main memory 1004, the static memory 1006, or the storage device 1016 may constitute machine-readable media.

While the machine-readable medium 1022 is illustrated as a single medium, the term "machine-readable medium" may include a single medium or multiple media (e.g., a centralized or distributed database, and/or associated caches and servers) configured to store the one or more instructions 1024.

Various embodiments may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "machine-readable medium" may include any medium that is capable of storing, encoding, or carrying instructions for execution by the machine 1000 and that cause the machine 1000 to perform any one or more of the techniques of the present disclosure, or that is capable of storing, encoding, or carrying data structures used by or associated with such instructions. Non-limiting machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., electrically programmable read-only memory (EPROM), or electrically erasable programmable read-only memory (EEPROM)) and flash memory devices; magnetic disks, such as internal hard disks and removable disks; magneto-optical disks; and CD-ROM and DVD-ROM disks.

The instructions 1024 may further be transmitted or received over a communications network 1026 using a transmission medium via the network interface device/transceiver 1020 utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), plain old telephone (POTS) networks, wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, and peer-to-peer (P2P) networks, among others. In an example, the network interface device/transceiver 1020 may include one or more physical jacks (e.g., Ethernet, coaxial, or phone jacks) or one or more antennas to connect to the communications network 1026. In an example, the network interface device/transceiver 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 1000 and includes digital or analog communications signals or other intangible media to facilitate communication of such software. The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

Some embodiments may be used in conjunction with various devices and systems, for example, a personal computer (PC), a desktop computer, a mobile computer, a laptop computer, a notebook computer, a tablet computer, a server computer, a handheld computer, a handheld device, a personal digital assistant (PDA) device, a handheld PDA device, an on-board device, an off-board device, a hybrid device, a vehicular device, a non-vehicular device, a mobile or portable device, a consumer device, a non-mobile or non-portable device, a wireless communication station, a wireless communication device, a wireless access point (AP), a wired or wireless router, a wired or wireless modem, a video device, an audio device, an audio-video (A/V) device, a wired or wireless network, a wireless area network, a wireless video area network (WVAN), a local area network (LAN), a wireless LAN (WLAN), a personal area network (PAN), a wireless PAN (WPAN), and the like.

Some embodiments may be used in conjunction with one way and/or two-way radio communication systems, cellular radio-telephone communication systems, a mobile phone, a cellular telephone, a wireless telephone, a personal communication system (PCS) device, a PDA device which incorporates a wireless communication device, a mobile or portable global positioning system (GPS) device, a device which incorporates a GPS receiver or transceiver or chip, a device which incorporates an RFID element or chip, a multiple input multiple output (MIMO) transceiver or device, a single input multiple output (SIMO) transceiver or device, a multiple input single output (MISO) transceiver or device, a device having one or more internal antennas and/or external antennas, digital video broadcast (DVB) devices or systems, multi-standard radio devices or systems, a wired or wireless handheld device, e.g., a smartphone, a wireless application protocol (WAP) device, or the like.

Some embodiments may be used in conjunction with one or more types of wireless communication signals and/or systems following one or more wireless communication protocols, for example, radio frequency (RF), infrared (IR), frequency-division multiplexing (FDM), orthogonal FDM (OFDM), time-division multiplexing (TDM), time-division multiple access (TDMA), extended TDMA (E-TDMA), general packet radio service (GPRS), extended GPRS, code-division multiple access (CDMA), wideband CDMA (WCDMA), CDMA 2000, single-carrier CDMA, multi-carrier CDMA, multi-carrier modulation (MDM), discrete multi-tone (DMT), Bluetooth®, global positioning system (GPS), Wi-Fi, Wi-Max, ZigBee, ultra-wideband (UWB), global system for mobile communications (GSM), 2G, 2.5G, 3G, 3.5G, 4G, fifth generation (5G) mobile networks, 3GPP, long term evolution (LTE), LTE advanced, enhanced data rates for GSM Evolution (EDGE), or the like. Other embodiments may be used in various other devices, systems, and/or networks.

Further, in the present specification and annexed drawings, terms such as "store," "storage," "data store," "data storage," "memory," "repository," and substantially any other information storage component relevant to the operation and functionality of a component of the disclosure, refer to memory components, entities embodied in one or several memory devices, or components forming a memory device. It is noted that the memory components or memory devices described herein embody or include non-transitory computer storage media that can be readable or otherwise accessible by a computing device. Such media can be implemented in any methods or technology for storage of information, such as machine-accessible instructions (e.g., computer-readable instructions), information structures, program modules, or other information objects.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language generally is not intended to imply that features, elements, and/or operations are in any way required for one or more implementations or that one or more implementations necessarily include logic for deciding, with or without user input or prompting, whether these features, elements, and/or operations are included or are to be performed in any particular implementation.

What has been described herein in the present specification and annexed drawings includes examples of systems, devices, techniques, and computer program products that, individually and in combination, certain systems and methods. It is, of course, not possible to describe every conceivable combination of components and/or methods for purposes of describing the various elements of the disclosure, but it can be recognized that many further combinations and permutations of the disclosed elements are possible. Accordingly, it may be apparent that various modifications can be made to the disclosure without departing from the scope or spirit thereof. In addition, or as an alternative, other embodiments of the disclosure may be apparent from consideration of the specification and annexed drawings, and practice of the disclosure as presented herein. It is intended that the examples put forth in the specification and annexed drawings be considered, in all respects, as illustrative and not limiting. Although specific terms are employed herein, they are used in a generic and descriptive sense only and not for purposes of limitation.

What is claimed is:

1. A system comprising:
   a processor; and
   a memory storing computer-executable instructions, that when executed by the processor, cause the processor to:
   receive a request for a vehicle from a mobile device of a user;
   receive, from a pathogen detector device within a first vehicle, an indication that a number of pathogens within the first vehicle is less than a threshold amount; and
   assign the first vehicle to the user based on the indication that the number of pathogens within the first vehicle is less than the threshold amount.

2. The system of claim 1, wherein the computer-executable instructions further cause the processor to:
   send a digital certificate indicating a cleanliness state of the vehicle to the vehicle for storage in a digital wallet of the vehicle.

3. The system of claim 1, wherein the computer-executable instructions further cause the processor to:
   receive, from the pathogen detector device, an indication that the number of pathogens within the first vehicle is greater than the threshold amount; and
   determine a second ride hail vehicle to assign to the user based on the determination that the number of pathogens within the first vehicle exceeds the threshold amount.

4. The system of claim 3, wherein the computer-executable instructions further cause the processor to:
   send an instruction for the first vehicle to travel to a cleaning location;
   determine that the first vehicle is at the cleaning location based on at least one of: a global positioning signal (GPS) signal from the first vehicle or an indication that a code associated with the first vehicle was scanned at the cleaning location; and
   determine, using the pathogen detector device within the first vehicle, that the first vehicle was cleaned.

5. The system of claim 3, wherein the computer-executable instructions further cause the processor to:
   present, determination that the number of pathogens within the first vehicle exceeds the threshold amount, a status indicator.

6. The system of claim 5, wherein presenting the status indicator includes changing a color of the status indicator, wherein the status indicator is presented on at least one of: the mobile device of the user, an interior of the first vehicle, or an exterior of the first vehicle.

7. The system of claim 1, wherein the computer-executable instructions further cause the processor to:
   store, using a smart contract associated with a Blockchain, an indication that the number of pathogens within the first vehicle is less than the threshold amount on the Blockchain.

8. The system of claim 1, wherein determining the number of pathogens within the first vehicle is based on a request from the user through the mobile device of the user, and wherein the threshold amount is based on a pre-established preference of the user.

9. A method comprising:
   receiving a request for a vehicle from a mobile device of a user;
   receiving, from a pathogen detector device within a first vehicle, an indication that a number of pathogens within the first vehicle is less than a threshold amount; and
   assigning the first vehicle to the user based on the indication that the number of pathogens within the first vehicle is less than the threshold amount.

10. The method of claim 9, further comprising:
    receiving, from the pathogen detector device, an indication that the number of pathogens within the first vehicle is greater than the threshold amount; and
    determining a second vehicle to assign to the user based on the determination that the number of pathogens within the first vehicle exceeds the threshold amount.

11. The method of claim 10, further comprising:
    sending an instruction for the first vehicle to travel to a cleaning location;
    determining that the first vehicle is at the cleaning location based on at least one of: a global positioning signal (GPS) signal from the first vehicle or an indication that a code associated with the first vehicle was scanned at the cleaning location; and
    determining, using the pathogen detector device within the first vehicle, that the first vehicle was cleaned.

12. The method of claim 10, further comprising:
    presenting, determination that the number of pathogens within the first vehicle exceeds the threshold amount, a status indicator.

13. The method of claim 12, wherein presenting the status indicator includes changing a color of the status indicator, wherein the status indicator is presented on at least one of: the mobile device of the user, an interior of the first vehicle, or an exterior of the first vehicle.

14. The method of claim 9, further comprising:
    storing, using a smart contract associated with a Blockchain, an indication that the number of pathogens within the first vehicle is less than the threshold amount on the Blockchain.

15. The method of claim 9, wherein determining the number of pathogens within the first vehicle is based on a request from the user through the mobile device of the user, and wherein the threshold amount is based on a pre-established preference of the user.

16. A non-transitory computer-readable medium storing computer-executable instructions, that when executed by a processor, cause the processor to:
    receive a request for a vehicle from a mobile device of a user;
    determine, using a pathogen detector device within a first vehicle, that a number of pathogens within the first vehicle is less than a threshold amount; and
    assign the first vehicle to the user based on the indication that the number of pathogens within the first vehicle is less than the threshold amount.

17. The non-transitory computer-readable medium of claim 16, wherein computer-executable instructions further cause the processor to:
    receiving, from the pathogen detector device, an indication that the number of pathogens within the first vehicle is greater than the threshold amount; and determine a second vehicle to assign to the user based on the determination that the number of pathogens within the first vehicle exceeds the threshold amount.

18. The non-transitory computer-readable medium of claim 17, wherein the computer-executable instructions further cause the processor to:

send an instruction for the first vehicle to travel to a cleaning location;

determine that the first vehicle is at the cleaning location based on at least one of: a global positioning signal (GPS) signal from the first vehicle or an indication that a code associated with the first vehicle was scanned at the cleaning location; and receive, from the pathogen detector device within the first vehicle, an indication that the first vehicle was cleaned.

19. The non-transitory computer-readable medium of claim 17, wherein the computer-executable instructions further cause the processor to:

present, determination that the number of pathogens within the first vehicle exceeds the threshold amount, a status indicator.

20. The non-transitory computer-readable medium of claim 16, wherein the computer-executable instructions further cause the processor to:

store, using a smart contract associated with a Blockchain, an indication that the number of pathogens within the first vehicle is less than the threshold amount on the Blockchain.

* * * * *